United States Patent [19]
Watson

[11] Patent Number: 6,020,071
[45] Date of Patent: Feb. 1, 2000

[54] LUBRICIOUS COATINGS

[75] Inventor: Jeremy Watson, 32 Fairview Road, Oxton, Birkenhead, Merseyside, 143 5UN, United Kingdom

[73] Assignee: Jeremy Watson, Birkenhead, United Kingdom

[21] Appl. No.: 08/973,250

[22] PCT Filed: Jun. 3, 1996

[86] PCT No.: PCT/GB96/01314

§ 371 Date: Nov. 26, 1997

§ 102(e) Date: Nov. 26, 1997

[87] PCT Pub. No.: WO96/39204

PCT Pub. Date: Dec. 12, 1996

[30] Foreign Application Priority Data

Jun. 3, 1995 [GB] United Kingdom ................. 9511233

[51] Int. Cl.⁷ ............................. B32B 27/40; B05D 3/02; B05D 5/08
[52] U.S. Cl. .................. 428/423.1; 424/422; 427/2.12; 427/2.3; 525/453; 525/454; 528/48; 528/52
[58] Field of Search .................... 427/2.28, 2.3, 427/2.12, 393.5, 421, 430.1; 428/423.1; 424/422; 525/453, 454; 508/239; 528/48, 52

[56] References Cited

U.S. PATENT DOCUMENTS

| | | | |
|---|---|---|---|
| 4,100,309 | 7/1978 | Micklus et al. | 427/2.28 |
| 4,729,914 | 3/1988 | Kliment et al. | 428/36 |
| 4,835,003 | 5/1989 | Becker et al. | 427/2.28 |
| 5,091,205 | 2/1992 | Fan | 427/2.28 |
| 5,290,585 | 3/1994 | Elton | 427/2.3 |
| 5,688,855 | 11/1997 | Stoy et al. | 524/505 |

FOREIGN PATENT DOCUMENTS

| | | |
|---|---|---|
| 0 454 293 A3 | 10/1991 | European Pat. Off. . |
| 89/05319 | 6/1989 | WIPO . |
| 94/21308 | 9/1994 | WIPO . |
| 94/23771 | 10/1994 | WIPO . |
| 95/06670 | 3/1995 | WIPO . |

*Primary Examiner*—Diana Dudash
*Attorney, Agent, or Firm*—Townsend and Townsend and Crew LLP

[57] ABSTRACT

A hydrophilic lubricious coating for an article comprising a non-toxic, cross-linked, hydrophilic polyurethane. The invention includes a method for preparing said lubricious coating, as well as a method for coating an article with said hydrophilic lubricious coating.

20 Claims, No Drawings

LUBRICIOUS COATINGS

The present invention concerns improvements in or relating to lubricious coatings and to methods of preparation thereof and application to the surface of a substrate. More particularly, the present invention relates to a hydrophilic lubricious coating which binds to the surface of, for example, medical instruments, such as, catheters, probes or feeding tubes, which instruments, in use, are inserted into a human or animal body cavity. Such hydrophilic lubricious coating aids passage of said medical instruments into such body cavity.

In order to reduce the surface coefficient of friction of such medical instruments, over the years, a number of coatings have been developed to be applied to such medical instruments and, hence, facilitate the insertion of such medical instruments into a human or animal body cavity with minimum discomfort being experienced by the user.

In this connection, jelly-like preparations have been smeared onto the surface of medical instruments before insertion into cavities of the body. However, a major disadvantage exhibited by such jelly-like preparations was that, on removal of such medical instruments from said body cavity, such jelly-like preparations were easily dislodged from the surface of said medical instruments and, consequently, resulted in a substantial degree of discomfort being experienced by the user. Moreover, residual jelly may remain within said body cavity which can produce a focus for subsequent infection.

Realising the disadvantages of the aforementioned jelly-like preparations, numerous types of hydrophilic lubricious coatings have subsequently been developed which bind to the surface of such medical instruments and, consequently, exhibit slipperiness when wet. Moreover, such hydrophilic lubricious coatings have also substantially increased the commercial value of said medical instruments.

Such hydrophilic lubricious coatings can be applied during manufacture of such medical instruments. However, the major disadvantage exhibited by such hydrophilic lubricious coatings is that the processes developed for applying such coatings to such medical instruments comprise numerous steps, which are time consuming and as a result thereof, large scale production is less financially beneficial. Further disadvantages of such coatings are that a high proportion of soluble material used washes off in use and therefore, the effective life span of said medical instruments is substantially reduced. Furthermore, some hydrophilic lubricious coatings exhibit roughness in their dry state and consequently, such roughness may be off-putting to the user.

One such method of making such a hydrophilic lubricious coating comprises dipping the medical instrument, such as a catheter, to be coated into diphenylmethane di-isocyanate (MDI) and allowing same to dry. Such medical instrument, with a dry coating of MDI, is then dipped into a hydrophilic agent, such as polyethylene oxide, which is also allowed to dry. Subsequently, both the MDI and the hydrophilic agent are heated in order that they may react resulting in the formation of the desirable hydrophilic coating. The major disadvantage of such a process is that on adding the MDI first, an excess of the hydrophilic agent must also be added in order to ensure that the coating is not over cross-linked, since this would prevent the coating being hydrophilic. However, too much hydrophilic agent may wash off in use and consequently, be left behind in the bladder which is undesirable. Moreover, the surface of said medical instrument is rough prior to wetting and is perceived as aesthetically poor quality.

It is object of the present invention to provide a hydrophilic lubricious coating for medical instruments, such as catheters, probes or tubes, which, in use, are inserted into a human or animal body cavity, which will at least minimise some of the disadvantages exhibited by the lubricious coatings outlined above. For example, the hydrophilic lubricious coating of the present invention can be applied.

In a single step to the surface of such medical instrument. Moreover, the composition of the present invention can be formulated to reduce the proportion of soluble material which may wash off in use and, consequently, the effective life span of such hydrophilic lubricious coating is substantially increased. Furthermore, the coating of the present invention exhibits smoothness in both the dry and wet states which may be preferable to the user.

According to one aspect of the present invention, there is provided a hydrophilic lubricious coating comprising a non-toxic, cross-linked, hydrophilic polyurethane coating which is insoluble in water, wherein said coating is formed from the reaction on a surface to be coated, of a mixture comprising an isocyanate terminated pre-polymer, formed from a polyether or polyester and an isocyanate, in a non-aqueous liquid and a hydrophilic diol having a molecular weight of 5000–30,000 in a non-aqueous liquid, and wherein the ratio, weight for weight, of pre-polymer to hydrophilic diol is 1:1 to 1:8.

Polyurethane is generally formed from a polyether, for example, polytetramethylene glycol which may have a molecular weight of 2000. Said glycol reacts with an isocyanate, for example, diphenylmethane di-isocyanate to form a pre-polymer comprising blocks of polyether or polyester capped with diphenylmethane di-isocyanate. Other di-isocyanates may be used. Said pre-polymer is then reacted with either a diamine, such as ethylene diamine or with a diol, such as 1:4 butanediol to extend the chain, length of said pre-polymer.

It is known that in order to make such polyurethane hydrophilic, the polytetramethylene glycol can be substituted by polyethylene oxide or polyethylene glycol. This is usually incorporated into the pre-polymer, wherein the length of the polyethylene glycol is restricted in order to prevent the final polymer becoming soluble. However, in the present invention it is the diol which is substituted by a hydrophilic diol having a very large molecular weight, for example, polyethylene glycol or polypropylene glycol. This would normally produce a polyurethane which is so soluble that it would dissolve in
water; however, in the present invention the ratio of pre-polymer to glycol is chosen such that in the reacting solution cross-linking occurs producing a hydrophilic polymer which is not soluble.

According to a further aspect of the present invention there is provided a hydrophilic lubricious coating, comprising adding a non-aqueous solution of an isocyanate terminated pre-polymer, said pre-polymer being formed from a polyether or polyester and an isocyanate, to a non-aqueous solution of a hydrophilic diol having a molecular weight of 5000–30,000 and wherein the ratio, weight for weight, of pre-polymer to hydrophilic diol is 1:1 to 1:8 such that when the two solutions react, cross-linking occurs to produce a hydrophilic polyurethane which is insoluble in water.

Preferably the hydrophilic diol is polyethylene glycol, although polypropylene glycol can also be utilised, if desired.

The molecular weight of the hydrophilic diol is generally in the range of 5000 to 30,000, with polyethylene glycol having a molecular weight of approximately 20,000 being particularly desired.

The ratio of pre-polymer to hydrophilic diol, weight for weight, is selected depending upon the nature of the substrate to which the lubricious coating is to be applied. Additionally, the selected ratio preferably ensures that there is excess pre-polymer present within the lubricious coating. Such excess pre-polymer forms further chemical cross-links with the substrate, thereby assisting in the formation of a relatively tough coating which has a longer life span. Accordingly, each particular lubricious coating is substrate specific and, depending upon the nature of the substrate to be coated, the ratio, weight for weight, of pre-polymer to hydrophilic diol utilised to form the hydrophilic cross-linked polyurethane may range from 1:1 to 1:8, preferably 1:2.

The pre-polymer is preferably used as a 2 to 20%, further preferably 10%, solution in a non-aqueous solvent such as tetrahydrofuran, methyl pyrrolidone or methylene chloride.

The hydrophilic diol is preferably used as a 2 to 20%, further preferably 10%, solution in a non-aqueous solvent such as dimethylformamide, dimethyl sulphoxide, dichloromethane or methyl pyrrolidone.

It is also possible to include a low molecular weight diol, into the coating composition of the present invention, the addition of such material generally assisting in causing the high molecular weight hydrophilic diol to dissolve in its organic solvent.

The lubricious hydrophilic coating of the present invention may also containing additional additives such as antimicrobial agents, for example, iodine or silver.

According to another aspect of the present invention there is provided a method of coating the surface of an article, suitably a medical instrument such as a catheter, tube or probe, comprising applying the lubricious coating of the present invention to the article, suitably by spraying or dip-coating and drying and curing the sprayed or coated article.

In a preferred embodiment the sprayed or coated article is suitably dried and cured at a temperature of from 60 to 100° C., preferably 80° C., for a period of approximately 10 to 30 minutes, usually 20 minutes.

The coated article is then allowed to cool and the coating can then be handled and, if desired, the article can be packed and, if necessary, sterilised utilising an appropriate sterilising agent such as ethylene oxide or by irradiation.

Further preferably, such medical instruments will comprise a suitable substrate to which the hydrophilic lubricious coating of the present invention will bind, such as PVC, polyurethane, nylon or latex.

The present invention will now be described in further detail with reference to the following example. The example is presented for the purposes of illustration only and not in a limiting sense.

EXAMPLE

A 10% solution of polyethylene glycol (molecular weight 20,000) dissolved in dimethylformamide, was mixed with a 10% solution of a pre-polymer known as AX-9192 and sold by Apollo Chemicals Ltd dissolved in tetrahydrofuran. Such solutions were mixed in a suitable proportion to produce a cross-linked polyurethane on reaction, viz. in a ratio of 2:1 of polyethylene glycol to pre-polymer, weight for weight.

The mixture is then applied to a substrate made of for example, polyurethane or PVC, by spraying or dip-coating. The coating is then dried and cured in an oven at a temperature of 80° C. for 20 minutes. After cooling, the coating can be handled and the device packed and sterilised.

Other pre-polymers which may be used are A7554 and A7153, both available from Apollo Chemicals Limited. The molecular weight of the polyethylene glycol may vary from 5000 to 30,000 and it is also possible to use polypropylene glycol and polypropylene oxide.

In friction tests which have been carried out, it has been found that the use of the lubricious coating in accordance with the present invention when applied on the surface of a medical instrument such as a catheter helps to reduce the surface coefficient of friction of said catheter: moreover, the coating remains firmly attached to the catheter.

Whilst the present invention has been generally described in relation to a hydrophilic lubricious coating for use on medical instruments, it is to be understood that such hydrophilic lubricious coating is also applicable in the case of any other implements which are desired to exhibit the same lubricious qualities of the hydrophilic coating of the present invention.

I claim:

1. A hydrophilic lubricious coating composition comprising a non-toxic, cross-linked hydrophilic polyurethane which is insoluble in water, wherein said polyurethane is formed from the reaction on a surface to be coated, of a mixture comprising (a) a solution of an isocyanate terminated pre-polymer in a non-aqueous liquid, said pre-polymer being formed from a polyether or a polyester and an isocyanate, and a solution of a hydrophilic diol having a molecular weight of 5000–30,000 in a non-aqueous liquid, wherein the ratio, weight for weight, of the pre-polymer to the hydrophilic diol is 1:1 to 1:8.

2. A hydrophilic lubricious coating composition as claimed in claim 1, wherein the hydrophilic diol is polyethylene glycol or polypropylene glycol.

3. A hydrophilic lubricious coating composition as claimed in claim 1, wherein the hydrophilic diol has a molecular weight of 20,000.

4. A hydrophilic lubricious coating composition as claimed in claim 1, wherein the ratio, weight for weight, of pre-polymer to hydrophilic diol is 1:2.

5. A hydrophilic lubricious coating composition as claimed in claim 1, wherein the concentration of the solution of the pre-polymer in the non-aqueous solvent is 2 to 20% be weight.

6. A hydrophilic lubricious coating composition as claimed in claim 5, wherein said non-aqueous solvent is tetrahydrofuran, methyl pyrrolidone or methylene chloride.

7. A hydrophilic lubricious coating composition as claimed in claim 1, wherein the concentration of the solution of the hydrophobic diol in the non-aqueous solvent is 2 to 20% by weight.

8. A hydrophilic lubricious coating composition as claimed in claim 7, wherein said non-aqueous solvent is dimethylformamide, dimethyl sulphoxide, dichloromethane or methyl pyrrolidone.

9. A method for preparing a hydrophilic lubricious coating composition, comprising:

(I) Adding (a) a non-aqueous solution of an isocyanate terminated pre-polymer, said pre-polymer being formed from a polyether or polyester and an isocyanate, to (b) a non-aqueous solution of a hydrophilic diol having a molecular weight of 5000–30000, wherein the ratio, weight for weight, of the pre-polymer to the hydrophilic diol is 1:1 to 1:8; and (II) Reacting, the two solutions (a) and (b) in (I) in a cross-linking reaction to produce a hydrophilic polyurethane which is insoluble in water.

10. A method for preparing a hydrophilic lubricious coating composition as claimed in claim 9, wherein the hydrophilic diol is polyethylene glycol or polypropylene glycol.

11. A method for preparing a hydrophilic lubricious coating composition as claimed in claim 9 or 10, wherein the hydrophilic diol has a molecular weight of 20,000.

12. A method for preparing a hydrophilic lubricious coating composition as claimed in claim 9, wherein the ratio, weight for weight, of pre-polymer to hydrophilic diol is 1.2.

13. A method for preparing a hydrophilic lubricious coating composition as claimed in claim 9, wherein the concentration of the solution of the pre-polymer in the non-aqueous solvent is 2 to 20% by weight.

14. A method for preparing a hydrophilic lubricious coating composition as claimed in claim 13, wherein said non-aqueous solvent is tetrahydrofuran, methyl pyrrolidone or methylene chloride.

15. A method for preparing a hydrophilic lubricious coating composition as claimed in claim 9, wherein the concentration of the hydrophilic diol in the non-aqueous solvent is 2 to 20% by weight.

16. A method for preparing a hydrophilic lubricious coating composition as claimed in claim 15, wherein said non-aqueous solvent is dimethylformamide, dimethyl sulphoxide, dichloromethane or methyl pyrrolidone.

17. A hydrophilic lubricious coating composition prepared by the method as claimed in claim 9.

18. A method of coating the surface of an article, comprising applying the lubricious coating as claimed in claim 1 to the surface of the article by spraying or dip-coating and drying and curing the sprayed or coated article.

19. A method of coating the surface of an article as claimed in claim 18, wherein the article is dried and cured at a temperature of 60 to 100° C., for a period of approximately 10 to 30 minutes.

20. An article coated by the method as claimed in claim 18.

* * * * *